United States Patent [19]

Crabb et al.

[11] Patent Number: 5,258,423
[45] Date of Patent: Nov. 2, 1993

[54] STABILIZATION OF METHACRYLIC POLYMERS AGAINST STERILIZING RADIATION

[75] Inventors: Charles C. Crabb, Mt. Holly, N.J.; Robert A. Wanat, Langhorne, Pa.; Paul J. Keating, Newportville, Pa.; Donald E. Roach, Willingboro, Pa.

[73] Assignee: Rohm and Haas Company, Philadelphia, Pa.

[21] Appl. No.: 60,849

[22] Filed: May 12, 1993

Related U.S. Application Data

[60] Continuation-in-part of Ser. No. 988,644, Dec. 10, 1992, which is a division of Ser. No. 751,421, Aug. 28, 1991, Pat. No. 5,216,060, which is a division of Ser. No. 499,104, Mar. 26, 1990, Pat. No. 5,102,940.

[51] Int. Cl.$^5$ ............................ C08K 5/04; C08K 9/00
[52] U.S. Cl. ..................................... 523/206; 524/379; 524/380
[58] Field of Search .................. 523/206; 524/379, 388

[56] References Cited

U.S. PATENT DOCUMENTS

| 2,129,478 | 9/1938 | Rohm | 260/2 |
|---|---|---|---|
| 3,879,495 | 4/1975 | Fujii et al. | 260/878 |
| 3,943,190 | 3/1976 | Abe | 525/380 |
| 4,056,559 | 11/1977 | Lewis et al. | 526/212 |
| 4,246,374 | 1/1981 | Kopchik | 525/329 |
| 4,415,706 | 11/1983 | Staas | 525/183 |
| 4,727,117 | 2/1988 | Hallden-Abberton et al. | 525/343 |
| 4,873,278 | 10/1989 | Nelson | 524/380 |
| 4,880,850 | 11/1989 | Nelson et al. | 522/79 |
| 5,061,747 | 10/1991 | Roach et al. | 524/379 |

FOREIGN PATENT DOCUMENTS 2169298 12/1985 United Kingdom .

OTHER PUBLICATIONS

On the Mechanism of Polymer Destruction under UV and Gamma Irradiation: The Influence of Low Molecular Weight Additives Related to Vibrational Cross-Relaxation, AS Belichenkol et al., Sixth Symposium on Radiation Chemistry (1986), pp. 535,538.
Effect of Low-Molecular-Weight Additives on the Radiation Strength of Transparent Polymers, E. Eremeeva et al., Sov. J. Opt. Technol., vol. 53, No. 6, Jun. 1986, pp. 361–362.

Primary Examiner—Joseph L. Schofer
Assistant Examiner—Jeffrey T. Smith
Attorney, Agent, or Firm—Roger K. Graham

[57] ABSTRACT

The present invention is directed to methacrylic polymer compositions which may be used to form plastic products which have increased resistance to discoloration by sterilizing radiation, such as gamma or electron beam irradiation. The compositions, free from conventional ultraviolet stabilizers, contain α-hydroxyacids or esters thereof.

11 Claims, No Drawings

STABILIZATION OF METHACRYLIC POLYMERS AGAINST STERILIZING RADIATION

This is a continuation-in-part of U.S. application Ser. No. 07/988,644, filed Dec. 10, 1992, which is a division of U.S. application Ser. No. 07/751,421, filed Aug. 28, 1991, now U.S. Pat. No. 5,216,060, which is a division of U.S. Ser. No. 07/499,104, filed Mar. 26, 1990 now U.S. Pat. No. 5,102,940.

BACKGROUND OF THE INVENTION

1. Field of the Invention

The present invention is directed to methacrylic polymer compositions which may be used to form plastic products which have increased resistance to sterilizing radiation. In particular, this invention relates to objects formed from poly(methyl methacrylate) which show maintenance of transparency and lack of yellowing on exposure to sterilizing radiation, such as gamma or electron beam irradiation, for sterilization purposes.

2. Description of the Prior Art

Poly(methyl methacrylate), including clear, impact modified forms, is a useful polymer for forming articles in the medical field, such as syringes, spikes, connectors and luers, suction devices, urine meters, blood plasma separators, drip chambers, cuvettes, dialyzer casings, chest drainage units, bottles for fluids, vaginal speculums, flow valves, aspirators, pump housings, containers for operating instruments, and the like, as the polymers are crystal clear, easily molded into the desired form, compatible with poly(vinyl chloride) (PVC) tubing, bondable to other plastics, resistant to deformation under warm conditions, reasonably tough and readily processed into useful objects. Such objects further have dimensional stability, have design flexibility, and can readily be disposed of after one-time use by incineration.

For many uses in the medical field, sterilization of these articles is required. Sterilization is often accomplished by exposure of the article to low level gamma or electron beam radiation (which will be designated "sterilizing radiation"). This sterilization is usually done for "use-once" or throw-away articles, although the invention would also apply to repeated sterilization.

The amount of radiation utilized to accomplish sterilization is well above "background" radiation, and when objects of polymerized methyl methacrylate are exposed to such radiation, the polymer is subject to yellowing. This yellowing reduces the light transmission of the poly(methyl methacrylate) and alters its appearance in an esthetically unfavorable way. Much of the yellow color will be lost on aging, especially if the sterilized sample is maintained at an elevated temperature, such as about 60° C., but the level of residual color is still unattractive when compared to the non-irradiated sample.

Poly(methyl methacrylate), although far less prone to discolor and lose properties on exposure to sunlight than other plastics, may be further stabilized against discoloration and loss of properties by use of any of a variety of ultraviolet stabilizers, such as benzotriazoles, hydroxyphenylbenzotriazoles, hindered amines, such as derivatives of 2,2,6,6-tetramethylpiperidine, salicylate esters, such as phenyl salicylate, o-hydroxybenzophenones, and the like. However, these materials are ineffective against discoloration by sterilizing radiation and certain ones may contribute further to the discoloration.

The art has also attempted to improve gamma radiation resistance of poly(methyl methacrylate) by addition of propyl alcohol. An article by A. S. Belichenkol et al, entitled "On the Mechanism of Polymer Destruction under UV and Gamma Irradiation: The Influence of Low Molecular Weight Additives Related to Vibrational Cross-Relaxation", Sixth Symposium on Radiation Chemistry, (1986), pages 535–538, discloses that polymer samples prepared by bulk radical polymerization of monomer compositions of methyl methacrylate which incorporated from 5 to 20% n-propyl alcohol showed improved resistance to gamma radiation, as judged by much slower development of UV-adsorbing chromophores. The large amounts of at least 5% propyl alcohol, however, would be expected to degrade the physical and mechanical properties of these polymers. This publication presents no comparative data between stabilized and non-stabilized polymers, but contrasts only irradiated and non-irradiated polymers of the same alcohol content in a qualitative statement.

Polymers of methyl methacrylate containing levels of alcohols less than 0.5%, insufficient effectively to inhibit yellowing on exposure to sterilizing radiation, have been known for some years. Recently, polymers of methyl methacrylate containing similar amounts of similar alcohols as described in the present invention have been found to be effective in resistance to ultraviolet degradation; such compositions are disclosed in U.S. patent application Ser. No. 385,139, incorporated herein by reference. It is well-known that commercial ultraviolet stabilizers in poly(methyl methacrylate) may protect against ultra-violet degradation but are ineffective or even produce higher color on exposure to sterilizing radiation, such as gamma irradiation. Thus, there is no reason to anticipate similar stabilization behavior for alcohol-containing poly(methyl methacrylate) on exposure to differing types of radiation of differing wave lengths and energy.

Thus, it would be desirable if poly(methyl methacrylate) could be provided which did not discolor on exposure to sterilizing radiation, while maintaining or only slightly decreasing its other desirable physical properties, and it is an object of the present invention to provide such poly(methyl methacrylate).

SUMMARY OF THE INVENTION

This invention is directed to a method for preparing a polymeric object with improved resistance to sterilizing radiation by first mixing one or more monomers wherein an alkyl methacrylate comprising at least 50% of the total monomer mix, with from about one-half to about two percent by weight of the monomers of at least one aliphatic alcohol of from one to ten carbon atoms, no ultraviolet stabilizer being present, an initiator of free-radical polymerization, and optionally a mercaptan chain transfer agent, then polymerizing the resulting mixture to form a polymer of at least 50% alkyl methacrylate units. The polymer may be used directly in the form in which it is polymerized; in other cases, it may be processed by methods well known to the art into an useful object resistant to sterilizing radiation.

The invention is further directed to a method where the alkyl methacrylate polymer is prepared separately and combined with the alcohol, no ultraviolet stabilizer being present, to form the desired blend, which is then processed by means well known to the art to form an useful object resistant to sterilizing radiation. It is further directed to a method wherein an impact modifier is admixed with the polymer prior to admixing the alcohol. It is further directed to a process for preparing useful sterilized objects by exposing such polymer/alcohol combinations to sterilizing radiation. The invention is further directed to useful objects requiring sterilizing such as containers, tubes, or medical tools prepared by such methods and exposed to sterilizing radiation.

The invention is further directed to the specific discovery that certain derivatives of lactic acid are effective when the total carbon count of the materials is above 10 carbon atoms, or when the amount of the certain lactate derivative is reduced to about 0.25% by weight of the monomers being polymerized. Thus lauryl lactate, containing 15 carbon atoms, is effective in preventing discoloration or retention of discoloration (i.e., the color from radiation fades more rapidly than for a control without stabilizer) under conditions where the corresponding aliphatic alcohol is not. Also, lactic acid (especially) and butyl lactate are found to be effective at levels of about 0.25%, which is an advantage because there is less deleterious effect on other performance properties, such as mold release.

DESCRIPTION OF THE INVENTION AND PREFERRED EMBODIMENTS

Having summarized the invention, the invention will now be discussed in detail by reference to the following specification and non-limiting examples.

By alkyl methacrylate is meant an alkyl, substituted alkyl, cycloalkyl, or substituted cycloalkyl ester of methacrylic acid. Such esters include alkyl, such as methyl, ethyl, butyl, octyl, stearyl, and the like, substituted alkyl, such as haloalkyl, hydroxyalkyl, and the like, for example 4-chlorobutyl, 2-fluoroethyl, 2-hydroxyethyl, and the like, cycloalkyl, such as cyclohexyl, isobornyl, fenchyl, and the like, and substituted cycloalkyl, such as 4-fluorocyclohexyl, and the like. Preferred are lower alkyl esters of from one to four carbon atoms, the cyclohexyl ester, and the isobornyl ester, as polymers containing these units have sufficiently high glass temperatures to be rigid, hard glasses at temperatures of room temperature and above. Especially preferred is methyl methacrylate for lower cost and ease of polymerization of the monomer, and for the high glass temperature and ease of impact modification of the resultant polymer. It is further preferred for reasons of good initial color, thermal stability and high service temperature of the resultant polymer that the amount of methacrylate ester be from about 90 to about 99 weight percent of the monomer mixture to be polymerized.

A variety of other monomers, such as vinyl or vinylidene monomers, may be copolymerized with the alkyl methacrylate esters, for example, vinyl aromatic monomers, such as styrene, alpha-methylstyrene, and the like, acrylate esters, such as alkyl acrylate esters, for example, methyl, ethyl, n-propyl, n-butyl, s-butyl, 2-ethylhexyl acrylate, and the like, (meth)acrylic acid, (meth)acrylonitrile, vinyl esters, such as vinyl acetate, maleimides, such as N-4-chlorophenyl maleimide and N-cyclohexyl maleimide, unsaturated acids, such as methacrylic acid, and the like. Preferred are the lower alkyl acrylates, wherein lower alkyl refers to 1 to 4 carbon atoms, for reasons of good clarity, good ultraviolet stability, and enhancement of thermal stability of the resultant polymer. Especially preferred is the use of from about 1 to about 10 weight percent of a lower alkyl ester of acrylic acid with a $C_1$ to $C_4$ primary alcohol.

The polymer derived from units mainly of alkyl methacrylate esters may be further reacted under conditions which introduce cyclic glutarimide or glutaric anhydride groups, and then stabilized against degradation by sterilizing radiation with alcohols similar to those effective with the polymers of the alkyl methacrylates.

By the term "alcohol containing up to 10 carbon atoms" is meant an aliphatic compound containing one or more hydroxyl groups of from 1 to 10 carbon atoms. Examples of such alcohols include monohydric alkyl alcohols, such as methanol, ethanol, n-propanol, i-propanol, s-butanol, t-butanol, 2-ethylhexanol, and the like; polyhydric alkyl alcohols, such as ethylene glycol, glycerine, trimethylolpropane, pentaerythritol, and the like; $\alpha$-hydroxyacids, such as lactic acid, and the like; and hydroxyesters, such as 2-hydroxyethyl acetate, diethylene glycol monoacetate, butyl lactate, butyl glycolate, and the like. Specifically noted is the behavior of esters of lactic acid even when they contain more than 10 carbon atoms, such as lauryl lactate, decyl lactate, 2-ethylhexyl lactate, and the like.

If the polymer during processing is to receive relatively little exposure to high heat, such as in casting and thermoforming a sheet, then the alcohol may be relatively volatile, such as methanol or ethanol. If the polymer is to be exposed to higher temperatures, such as polymerization at temperatures well above 100 degrees C., to devolatilization at such temperatures under vacuum or autogeneous pressure, such as devolatilization of a monomer-polymer syrup or of a solution of polymer and monomer in a high-boiling solvent, or to high temperatures of processing, such as extrusion, then the alcohol should be high enough boiling so as not to be driven out during the processing steps. Alternatively, the alcohol may be added late in the sequence of processing steps, such as just prior to extrusion or molding of the final article.

For some uses where the resulting polymer will be exposed to sterilizing radiation, the polymer may be in the form of a sheet formed by "casting", which is bulk polymerization of the monomers between glass or metal surfaces, followed by optional thermoforming of the resulting sheet. For these purposes, the molecular weight of the polymer needs be above a minimum value where embrittlement may set in, such as about 20,000 weight-average molecular weight. Such cell-casting is a useful means for forming sheets later processed into useful objects, such as covers, viewing ports, containers, and the like, by thermoforming.

Especially useful in processes where molding is not utilized are cell-casting methods where essentially no residual monomer remains, which can be achieved by appropriate selection of initiators and polymerization times and temperatures.

Analogous to cell-casting methods are other methods wherein the polymerization is conducted in bulk, such as in poly(vinyl alcohol) bags, and the polymer processed in an extruder to form molding pellets. Any residual monomer may be removed by devolatilization during such pelletization, and alcohol may be added at that time, along with other additives.

Further, imidized derivatives of poly(alkyl methacrylates), especially poly(methyl methacrylate), may also be protected against yellowing by sterilizing radiation by the addition of the alcohols of the present invention.

By "imidized" is meant the polymer formed when an poly(alkyl methacrylate) is reacted with ammonia or an alkyl amine under pressure in an extruder to introduce cyclic units of the formula

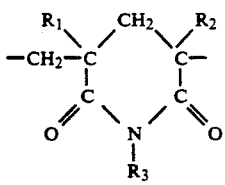

where $R^1$ and or $R^2$ are $CH_3$ and $R^3$ is H or alkyl. Such thermally stable polymers and their preparation are disclosed in Kopchik, U.S. Pat. No. 4,246,374. Such polymers, which often also contain cyclic anhydride and free acid groups, may be further treated with alkylating agents to remove acid and anhydride functionality, as taught by Hallden-Abberton et al., U.S. Pat. No. 4,727,117. Imidized polymers may be prepared by other methods known in the literature, as long as they meet the thermal stability criteria of Kopchik. The molecular weight of the polymer containing glutarimide units is preferably from 100,000 to 500,000, but polymers outside this molecular weight range stabilized with aliphatic alcohols may be useful in certain applications requiring sterilization.

As the imidized polymers undergo high temperatures and devolatilization during their preparation, it is preferable to add the alcohols and other additives to the melt after cyclization and alkylation have been completed. The alcohols to be added are those useful in combination with the poly(alkyl methacrylates) and are employed at similar levels.

The polymers containing glutarimide units will exhibit a higher service temperature than the (meth)acrylate polymers from which they are derived, and may be molded into useful objects, especially for use at high service temperature, such as lamp covers, automotive headlight covers, glazing, and the like. They may be molded into objects which require sterilization in a manner similar to the methacrylic polymers taught above. They are especially useful where heating and sterilization are required.

In a similar manner, units derived from glutaric anhydride may be incorporated into the polymer by methods known to the art, especially by treating the poly(alkyl methacrylate) with dimethyl amine in an extruder, as taught by Hallden-Abberton et al., U.S. Pat. No. 4,874,824. Care must be taken in admixing the stabilizing alcohol that reaction does not occur with the anhydride ring.

For most purpose, the polymer will be shaped into a form which may be best achieved by injection-molding. In that case, the polymer weight should not be excessive. A useful range is from about 20,000 to about 300,000, but a preferred range is from about 80,000 to about 150,000. Such molecular weight control may be achieved by control of the polymerization conditions, especially by the use of chain transfer agents. Use of an alkyl mercaptan, such as n-dodecyl mercaptan, at levels from about 0.01 to 0.5 weight percent, is preferred. Presence of the mercaptan, which during polymerization is chemically combined into the polymer in the form of a terminal sulfide group, is not detrimental to the stabilizing effect of the alcohol.

Polymers useful in this application may be prepared by many means other than cell- or bulk-casting. Such methods include suspension, emulsion, solution, and continuous bulk polymerization.

For many of the envisioned medical or other sterilizable uses, the toughness of the methacrylate polymer may not be sufficient. Known impact modifiers for methacrylate polymers may be added, such as polyurethane rubbers, graft polymers of methyl methacrylate or styrene/acrylonitrile to ethylene-propylene or ethylene-propylene-diene terpolymers, graft polymers of methyl methacrylate or methyl methacrylate/styrene or styrene/acrylonitrile onto butadiene-based rubbers, such as poly(butadiene) or butadiene-styrene or butadiene-acrylonitrile copolymers, or staged copolymers of styrene-acrylonitrile or of methyl methacrylate polymers onto a first stage of a alkyl acrylate or alkyl acrylate/styrene polymer. Most of these impact modifiers will be discolored and/or will suffer chemical changes as the result of exposure to sterilizing radiation, even when surrounded by the poly(methacrylate) matrix. For this reason, preferred for uses requiring exposure to sterilizing radiation are those impact modifiers containing almost exclusively units derived from alkyl esters of methacrylic and acrylic acids. More preferred, as the main uses for such sterilized articles requires transparency, are those impact modifiers designed to retain the clarity of the poly(methacrylate) matrix, accomplished by control of refractive index and particle size of the various impact modifier components, such as by matching the refractive index of all components of the multistage polymer to that of the matrix polymer. Especially preferred for avoidance of discoloration during processing or exposure to various forms of radiation are those polymers based on a first stage of butyl acrylate copolymerized with styrene, optionally containing multifunctional monomers, such as glycol esters of acrylic or methacrylic acid, diallyl esters of maleic acid, allyl esters of methacrylic or acrylic acid, and the like, and a final stage of methyl methacrylate or of a copolymer rich in methyl methacrylate. Also especially preferred are those polymers having a hard core of a poly(alkyl methacrylate), an intermediate stage of butyl acrylate copolymerized with styrene, optionally containing multifunctional monomers, such as glycol esters of acrylic or methacrylic acid, dially esters of maleic acid, allyl esters of methacrylic or acrylic acid, and the like, and a final stage of methyl methacrylate.

The impact modifier may be blended at the solids stage or in the molten state with the polymer of the alkyl methacrylate, or, if prepared in emulsion, may be admixed in emulsion form and co-coagulated, such as in a kettle or in an extruder. Further, the impact modifier may be added to a molten mixture of polymer and residual monomer, and the residual monomer concurrently devolatilized. The alcohol may be added at various stages of these processes, depending on its boiling point, and the temperatures, pressures, and times encountered.

The polymer may also contain conventional low levels of lubricants, such as stearyl alcohol, stearic acid, butyl stearate, and the like. It should be noted that stearyl alcohol, which is not a C1 to C10 alkyl alcohol, is not effective in promoting resistance to color formation by sterilizing radiation. Other ultraviolet stabilizers may also be present, but if present, testing must be conducted to show that they do not cause discoloration on exposure to sterilizing radiation. Since the alcohols are effective ultraviolet stabilizers, it is generally not necessary to add a second ultraviolet stabilizer.

The polymers containing the stabilizers may be converted into useful objects by a variety of methods including injection molding, injection blow molding, extrusion blow-molding, calendering, thermoforming, profile extrusion, sheet extrusion, vacuum-assisted thermoforming, and the like. For many uses, especially in medical devices, injection molding is the method of choice. As the low level of alcohol has little effect on the rheological and other processing characteristics of the polymer, conventional means and techniques for processing the alkyl methacrylate polymer may be employed.

Sterilization of the formed objects may be accomplished by exposure to various forms of irradiation. Most often used are beta- and gamma-sources. The beta source delivers electrons to the object, and of several commercially available sources may be used. Most doses are delivered rapidly with concurrent heat build-up, so gamma radiation, which is slower and where the temperature of the object may be better controlled, is preferred. Gamma rays arise from decay of materials such as cobalt-60, and exposure to such sources may be achieved in a air, water, or nitrogen atmosphere. Doses are controlled by the time of exposure.

Measurement of the effect on color is conducted by means well known to the art. The total light transmittance and haze (ASTM D-1003) may be measured to quantify the retention of clarity. Standard means for measuring and reporting yellowness index changes (ASTM D-1005) measures the color changes which occur, even if transmittance is less stringently effected.

EXAMPLE 1

This example describes the preparative means for copolymers of methyl methacrylate/ethyl acrylate to be subjected to sterilizing radiation. In these mixtures, the mercaptan present in the mix was incorporated into the polymer chain; it was present to control and lower the molecular weight so that the resultant polymer can be injection molded. The C16-C18 alcohols were present as release agents when the polymer was injection molded.

In process A, a mixture of 94 parts methyl methacrylate (MMA), 5 parts ethyl acrylate (EA), 0.472 parts n-dodecylmercaptan (n-DDM), 0.5 parts of a cetyl-stearyl alcohol (C16-C18 mixture), 0.01 parts of azo(-bisisobutyronitrile)(AIBN), 0.01 parts of t-butyl peroxypivalate, 0.01 parts of t-butyl peroxyacetate, and the selected amount of stabilizing alcohol were mixed. The mixture was degassed, charged to poly(vinyl alcohol) bags, and polymerized in an oven at 60 degrees C. until any exotherm has subsided, then at 80 degrees C. for four hours, and then at 120 degrees C. for at least four hours. The bags were stripped from the polymer, the polymer broken into small pieces, and fed to an extruder equipped with a strand die and strand cutter to prepare pellets for molding. Pellets were molded in a ASTM molds under conditions recommended for commercial acrylic molding powders into test bars of 3.18 mm. thickness. For a reciprocating screw machine, samples would be dried at 87 degrees C. to remove any water, and processed at a melt temperature ca. 230 degrees C., and a mold temperature of ca. 65 degrees C.

In process B, a higher molecular weight cast sheet was prepared. A mixture of MMA 96, EA 4, AIBN 0.0075, and the alcohol was degassed, charged between glass plates separated by a 4.75 mm. vinyl spacer, the gasket seal closed, and the mixture heated at 66 degrees C. overnight, followed by polymerization "finish-off" similar to process A. The plate glass was removed to yield a casting for irradiation.

In process C, a polymer of MMA/EA ca. 95.5/4.5 obtained as a commercial molding resin free from any ultraviolet stabilizer was processed in a twin screw extruder and a mixture of 1 part butyl lactate in 2 parts ethanol was added to the melt. The melt was stranded, cut into pellets, and remolded as in process A; in this case both 3.18 (Example 11) and 4.75 mm. (Ex. 12) thick bars were obtained for irradiation.

EXAMPLES 2-12

In these examples are described the actual formulations studied (Table I) and the results of exposure to a targeted exposure of three Megarads (actual dosage 2.84 to 2.98 Megarads) of gamma irradiation at a commercial source of unknown configuration (Table II). The optical methods for measurement are described earlier. Parts of alcohol are in addition to the parts of monomer, etc. described in Example I. EG is ethylene glycol, BL is butyl lactate. Certain examples (4, 7, 10) contain higher levels of alcohol, and are plasticized by that level so as to lower service temperature and modulus, although imparting an even higher degree of stabilization to sterilizing radiation. In all cases shown, the low level of alcohol used produces a very significant advantage in resistance to yellowing.

TABLE I

Formulations Containing Alcohol

| Example | Polymer from Process | Alcohol I, parts | Alcohol II, parts | Other alcohols |
|---|---|---|---|---|
| 2 | A (control) | — | — | |
| 3 | A | EG, 1 | glycerine, 1 | |
| 4 | A (excess) | EG, 1 | glycerine, 1 | t-butanol, 5; BL 5. |
| 5 | B (control) | — | — | — |
| 6 | B | methanol, 2 | — | — |
| 7 | B (excess) | methanol, 5 | — | — |
| 8 | B | ethanol, 2 | — | — |
| 9 | B | i-propanol, 2 | — | — |
| 10 | B (excess) | i-propanol, 5 | — | — |
| 11 | C | ethanol, 2 | BL, 1 | |
| 12 | C | ethanol, 2 | BL, 1 | |

TABLE 2

Optical Property Data After Exposure to 3 Mrad Gamma Radiation

| Sample ID | Thick | % Transmission 300 nm | % Transmission 340 nm | Δ % Transmission 300 nm | Δ % Transmission 340 nm | YI | YI |
|---|---|---|---|---|---|---|---|
| Ex. 2 | 0.120* | 49.8 | 77.7 | — | — | +1.6 | — |
| (Control) | 0.121 | 0.5 | 27.3 | −49.3 | −50.4 | +11.1 | +9.6 |
| | 0.120 | 0.6 | 27.6 | −49.2 | −50.1 | +11.0 | +9.4 |
| | 0.120 | 0.6 | 27.8 | −49.2 | −49.9 | +10.9 | +9.3 |
| Ex. 3 | 0.125* | 56.0 | 78.8 | — | — | +2.0 | — |
| | 0.125 | 26.8 | 69.6 | −29.2 | −9.2 | +3.1 | +1.0 |
| | 0.125 | 26.8 | 69.4 | −29.2 | −9.4 | +3.0 | +1.0 |
| | 0.125 | 27.5 | 69.7 | −28.5 | −9.1 | +3.0 | +1.0 |
| Ex. 4 | 0.123* | 59.1 | 83.2 | — | — | +1.4 | — |
| (Excess) | 0.123 | 54.4 | 80.9 | −4.7 | −2.3 | +1.5 | +0.1 |
| | 0.123 | 55.0 | 81.1 | −4.1 | −2.1 | +1.5 | +0.1 |
| | 0.123 | 54.8 | 80.8 | −4.3 | −2.4 | +1.5 | +0.1 |
| Ex. 5 | 0.187* | 80.0 | 89.5 | — | — | +0.7 | — |
| (Control) | 0.187 | 0.4 | 13.7 | −79.6 | −75.8 | +14.9 | +14.2 |
| Ex. 6 | 0.187* | 84.6 | 89.8 | — | — | +0.8 | — |
| | 0.187 | 36.3 | 78.1 | −48.3 | −11.7 | +1.7 | +0.9 |
| Ex. 7 | 0.187* | 82.9 | 90.0 | — | — | +0.8 | — |
| (Excess) | 0.187 | 61.6 | 86.8 | −21.3 | −3.2 | +0.6 | −0.2 |

TABLE 2-continued

Optical Property Data After Exposure to 3 Mrad Gamma Radiation

| Sample ID | Thick | % Transmission 300 nm | % Transmission 340 nm | Δ % Transmission 300 nm | Δ % Transmission 340 nm | YI | YI |
|---|---|---|---|---|---|---|---|
| Ex. 8 | 0.187* | 83.6 | 89.5 | — | — | +0.9 | — |
|  | 0.187 | 39.9 | 77.9 | −43.7 | −11.6 | +1.5 | +0.6 |
| Ex. 9 | 0.187* | 84.2 | 89.2 | — | — | +0.9 | — |
|  | 0.187 | 20.3 | 65.9 | −63.9 | −23.3 | +2.8 | +1.9 |
| Ex. 10 | 0.187* | 82.6 | 89.8 | — | — | +0.9 | — |
| (Excess) | 0.187 | 53.6 | 86 | −29.0 | −3.8 | +0.9 | 0 |
| Ex. 11 | 0.125* | 79.6 | 87.3 | — | — | +0.8 | — |
|  | 0.125 | 27.8 | 70.8 | −51.8 | −16.5 | +2.4 | +1.6 |
| Ex. 12 | 0.187* | 69.2 | 84.8 | — | — | +1.0 | — |
|  | 0.187 | 13.4 | 60.4 | −56.0 | −24.4 | +3.4 | +2.4 |

*not exposed to radiation

EXAMPLE 13

An impact modifier of the composition of Example 8 of Owens, U.S. Pat. No. 3,793,402, was prepared in emulsion by the method taught by Owens, was isolated by spray-drying, and was blended with a equivalent amount of poly(methyl methacrylate) molding powder of MW ca. 110,000 as taught in Example 1 of Owens. No UV stabilizer was present. The blend was prepared on a single screw Killion extruder of 38.1 mm. diameter. at a melt temperature of 218 degrees C.

To the blend was added in the melt stage various levels (0.5, 1, and 2.5 wt. %) of butyl lactate. Extrusion was conducted for a long enough time to purge any overlap of samples. Prior to the addition of the butyl lactate, enough polymer blend free of alcohol was extruded to serve as a control. The samples were molded into test pieces as in Example 1, but at a melt temperature of 220 degrees C. and a mold temperature of 76 degrees C. These are conditions similar to those recommended for commercial impact-modified acrylic plastics.

Exposure to ca. 3 MRads of gamma irradiation, as in Example 1, demonstrated less color formation and better retention of transmission of UV and visible light for the samples containing the butyl lactate.

EXAMPLE 14

A mixture of methyl methacrylate 95.26, ethyl acrylate 4.5, and n-dodecyl mercaptan 0.22% was polymerized in a continuous flow, stirred tank reactor with an organic peroxide to ca. 50% conversion, the polymer-monomer mixture pumped to a devolatilizing twin-screw extruder where residual monomer was removed, and then various levels of butyl lactate (BL) admixed with the molten polymer. Samples were prepared with 0% (control), 1%, 2%, and 5% BL. The polymers were stabilized were conveyed by the extruder to an extruding die, and the polymers stranded and cut into pellets. Materials were molded for exposure to sterilizing irradiation and physical testing as in Example 1. Exposure to ca. 3 MRads of gamma irradiation, as in Example 1, demonstrated less color formation and better retention of transmission of UV and visible light for the samples containing the butyl lactate.

EXAMPLES 15-20

These examples illustrates formulations of a polyglutarimide stabilized against sterilizing radiation by aliphatic hydroxy compounds. A poly(methyl methacrylate) of molecular weight ca. 150,000 is treated with methylamine in an extruder and then post-treated to reduce the content of acid and anhydride groups in a manner similar to Example 32 of U.S. Pat. No. 4,727,117. The Vicat softening temperature of the resultant polymer is ca. 145 degrees C. One preparation contains no stabilizer; a second preparation contains 0.15 weight percent of tris(nonylphenyl phosphite) and 0.25 weight percent of a commercial ultraviolet stabilizer, 2-(2-hydroxy-5-t-octylphenyl)benzotriazole, added after the post-treatment but prior to stranding and pelletizing.

The pellets of polymer are blended with either ethylene glycol or butyl lactate (1.2 weight percent on polymer), and then re-extruded in a single screw extruder at a set temperature of 232 degrees C., and the pellets are molded into appropriate test pieces at a melt temperature of 280 degrees C. and a mold temperature of 104 degrees C. The control with no additives is molded directly from pellets, and so has received less thermal history. The test pieces are exposed to gamma radiation as in Example 1.

| Example | Weight Percent TNPP | C-5411 | EG | BL |
|---|---|---|---|---|
| 15 | 0.15 | 0.25 | — | — |
| 16 | 0.15 | 0.25 | 1.2 | — |
| 17 | 0.15 | 0.25 | — | 1.2 |
| 18 | — | — | 1.2 | — |
| 19 | — | — | — | 1.2 |
| 20 | — | — | — | — |

TNPP is tris(nonylphenyl)phosphite; C-5411 is 2-(2-hydroxy-5-t-octylphenyl)benzotriazole; EG is ethylene glycol; BL is butyl lactate.

EXAMPLES 21-28

The method of Example 8 was followed with various additives, their level being adjusted in Examples 22-27 to give a mol percent of stabilizer equivalent to one weight percent of the butyl lactate control. The formulations are reported in weight percent of the stabilizing additive. The plaques were then exposed to a targeted exposures of 5 megarads of gamma radiation (as in Examples 2-13), and color development and time to fade recorded qualitatively. Examples 22, 23, and 27 relate to the additional claimed material of the present application; Examples 24, 25, 26, and 28 are outside the present invention. In Example 28-A hydroxyethyl methacrylate (HEMA) at the 1 weight percent level was copolymerized into the PMMA matrix, and, in Example 28-B, copolymerized into the outer stage of the impact modifier.

| Example | Additive | Wt. % | Color Development/Retention |
|---|---|---|---|
| 21 | none | — | moderate/slow to fade |
| 22 | butly lactate | 1.0 | low/rapid to fade |
| 23 | butyl glycolate | 0.90 | some/less rapid to fade |
| 24 | butyl propionate | 0.89 | as in Example 21 (no effect) |
| 25 | ethyl phenylacetate | 1.12 | as in Example 21 (no effect) |
| 26 | calcium lactate | 1.05 | as in Example 21 (no effect) |
| 27 | lactic acid | 0.62 | low/rapid to fade |
| 28-A | HEMA in matrix | 1.0 | as in Example 21 (no effect) |
| 28-B | HEMA in modifier | 1.0 | as in Example 21 (no effect) |

EXAMPLES 29-42

Polymers were prepared as in Example 8, except that the level of impact modifier (calculated here as core/shell polymer only) was varied from 40 parts down to 20 parts of the blend, and the additives imparting sterilization resistance were compounded into the polymer after its preparation. Such re-compounding will affect the initial yellowness relative to moldings from commercial polymers. Plaques (0.125 inches, 3.18 mm. thick) were exposed to 5000-volt electron radiation as dosages of 2.5, 5.0 and 7.5 megarads. Yellowness was determined both directly after exposure and after 5, 10 and 30 day recovery periods. Samples relating to the present invention were treated with 0 (control), 0.25, 0.5, 0.75 and 1.0% of butyl lactate (BL) or of lactic acid (LA). Tin. P is Tinuvin-P, a hydroxyphenylbenzotriazole ultra-violet stabilizer which discolors under electron-beam irradiation. Examples 31, 32, and 35-43 further contained less than 1% of a styrene/acrylonitrile copolymer for improved refractive index match between matrix and impact modifier. Stearyl alcohol (0.6%) was present as a lubricant in Example 36, and stearic acid (0.3 to 0.7%) in Examples 29-32. Less than 1 ppm of toner was present in Examples 29-34.

Samples Which Were Treated With Electron-Beam Irradiation

| Example | Matrix | Amount IM | Additive |
|---|---|---|---|
| 29 | 87/13 | — | — |
| 30 | 95/5 | — | 0.0075 Tin. P |
| 31 | 91/9 | 20 | — |
| 32 | 91/9 | 40 | — |
| 33 | 95/5 | 40 | — |
| 34 | 95/5 | 40 | 0.075 Tin. P |
| 35 | 91/9 | 20 | BL, 0.9% |
| 36 | 91/9 | 40 | BL, 1% |
| 37 | 91/9 | 40 | BL, 0.25% |
| 38 | 91/9 | 40 | BL, 0.50% |
| 39 | 91/9 | 40 | BL, 0.75% |
| 40 | 91/9 | 40 | LA, 0.25% |
| 41 | 91/9 | 40 | LA, 0.5% |
| 42 | 91/9 | 40 | LA, 0.75% |
| 43 | 91/9 | 40 | LA, 1.0% |

Initial Color And Color After Irradiation

| Example | Dose, megarads | Color Before Treatment | 1 day | 5 days | 10 days | 30 days |
|---|---|---|---|---|---|---|
| 29 | 7.5 | <1 | 16 | 15 | 13 | 7 |
| 30 | 7.5 | <1 | 23 | 22 | 20 | 17 |
| 31-A | 2.5 | 1.5 | 12 | 12 | 10 | 8 |
| 31-B | 7.5 | 1.5 | 16 | 14 | 12 | 10 |
| 32-A | 2.5 | <1 | 11 | 11 | 10 | 7 |
| 32-B | 7.5 | <1 | 15 | 13 | 11 | 8 |
| 33-A | 2.5 | <1 | 10 | 11 | 11 | 10 |
| 33-B | 7.5 | <1 | 16 | 15 | 14 | 11 |
| 34 | 7.5 | <1 | 53 | 50 | 48 | 45 |
| 35-A | 2.5 | 1 | 6.5 | 2.5 | 2.0 | 1.5 |
| 35-B | 7.5 | 1 | 4.5 | 2.5 | 1.5 | 1.5 |
| 36-A | 2.5 | 1.5 | 6 | 3 | 2 | 2 |
| 36-B | 7.5 | 1.5 | 4 | 2.5 | 2 | 2 |
| 37 | 7.5 | 1.5 | 9 | 7 | 5 | 3.5 |
| 38 | 7.5 | 1.5 | 6 | 4 | 3 | 2.5 |
| 39 | 7.5 | 1.5 | 5 | 3.5 | 2.5 | 2 |
| 40 | 7.5 | 2.5 | 5.5 | 4 | 3 | 2.5 |
| 41 | 7.5 | 2 | 4 | 3 | 2.5 | 2 |
| 42 | 7.5 | 2 | 3.5 | 2.5 | 2 | 2 |
| 43 | 7.5 | 2 | 3 | 2.5 | 2 | 2 |

The data support the stabilizing influence of butyl lactate and lactic acid, especially at levels of 0.5 to 1 weight percent, on decreasing discoloration and improving recovery time after exposure to sterilizing electron-beam irradiation, Of note is the lowered yellowing at higher doses for the stabilized samples, the more rapid decay of any induced color for the stabilized samples, and the fact that, unlike the gamma-irradiated sample, the electron beam sterilized stabilized samples did not completely return to their initial very low color, although the color should be satisfactory for commercial sterilization purposes.

EXAMPLE 44

The experiment of Example 22 was repeated but with an equimolar amount (2.3 weight percent) of lauryl lactate, and the results were similar to those found with 1 weight percent butyl lactate, i.e., low color development vs. a control and more rapid fading of the color.

EXAMPLE 45

A commercially available clear polymer useful for packaging purposes, known as Cyro® ™ G20-HiFlo, appears to be based on a matrix resin which is a copolymer of methyl methacrylate 59/ styrene 41, impact-modified with a butadiene-rubber based impact modifier. The amounts, if any, of ultraviolet stabilizer and toner are unknown.

The polymer was blended with 2.0 weight percent butyl lactate and exposed, along with a control, to 5 megarads of sterilizing gamma irradiation. The polymer containing butyl lactate developed much less color, and the fading of color was more rapid, than for the control polymer.

We claim:
1. A container, tube, or medical tool with improved resistance to sterilizing radiation formed by the process of:
   a. preparing a polymer comprising at least 50% of units derived from one or more alkyl methacrylate monomers and, optionally, one or more other monomers selected from vinyl or vinylidene monomers;
   b. admixing the polymer with up to about 50 weight percent, based on the polymer, of an impact modifier for the polymer;
   c. admixing the polymer-impact modifier mixture with from about 0.25 to about two percent by weight of the polymer of at least one α-hydroxyacid, no ultraviolet stabilizer being present, so as to distribute the α-hydroxyacid essentially uniformly throughout the polymer;
   d. forming the polymer-impact modifier-α-hydroxyacid mixture into a container, tube, or medical tool.
2. The container, tube or medical tool of claim 1 wherein the α-hydroxyacid is lactic acid and the amount is from about 0.25 to less than 0.5 percent by weight of the polymer.
3. A sterilized container, tube, or medical tool prepared by the process of:
   a. preparing a polymer comprising at least 50% of units derived from one or more alkyl methacrylate monomers and, optionally, one or more other monomers selected from vinyl or vinylidene monomers;
   b. admixing the polymer with up to about 50 weight percent, based on the polymer, of an impact modifier for the polymer;
   c. admixing the polymer-impact modifier mixture with from about 0.25 to about two percent by weight of the polymer of at least one α-hydroxyacid, no ultraviolet stabilizer being present, so as to distribute the α-hydroxyacid essentially uniformly throughout the polymer;

d. forming the polymer-impact modifier-α-hydroxyacid mixture into a container, tube, or medical tool;

e. exposing the container, tube, or medical tool to at least about 3 megarads of gamma irradiation or to at least about 2.5 megarads of elctron beam sterilizing radiation.

4. The container, tube or medical tool of claim 3 wherein the α-hydroxyacid is lactic acid and the amount is from about 0.25 to less than 0.5 percent by weight of the polymer.

5. The container, tube, or medical tool of claim 1 wherein the impact modifier is a core/shell polymer containing a core primarily of units derived from butyl acrylate.

6. The container, tube, or medical tool of claim 5 wherein the impact modifier is a core/shell polymer containing a hard core predominantly of units derived from methyl methacrylate, and intermediate stage predominantly of units derived from butyl acrylate, and a shell predominantly of units derived from methyl methacrylate.

7. The container, tube, or medical tool of claim 1 wherein the polymer prior to addition of the impact modifier and the α-hydroxyacid is in molten form or in solution.

8. The container, tube, or medical tool of claim 7 wherein the temperature of the admixture of the impact modifier and of the α-hydroxyacid is from about 200° C. to about 250° C.

9. A container, tube, or medical tool with improved resistance to sterilizing radiation formed by the process of:

a. preparing a polymer comprising at least 50% of units derived from one or more alkyl methacrylate monomers and, optionally, one or more other monomers selected from vinyl or vinylidene monomers;

b. admixing the polymer with up to about 50 weight percent, based on the polymer, of an impact modifier for the polymer;

c. admixing the polymer-impact modifier mixture with from about one-half to about two percent by weight of the polymer of an ester of an α-hydroxyacid, the ester containing from above 10 to 25 carbon atoms, no ultraviolet stabilizer being present, so as to distribute the ester essentially uniformly throughout the polymer;

d. forming the polymer-impact modifier-ester mixture into a container, tube, or medical tool.

10. The container, tube or medical tool of claim 9 wherein the ester of the α-hydroxyacid is lauryl lactate.

11. A sterilized container, tube, or medical tool prepared by the process of:

a. preparing a polymer comprising at least 50% of units derived from one or more alkyl methacrylate monomers and, optionally, one or more other monomers selected from vinyl or vinylidene monomers;

b. admixing the polymer with up to about 50 weight percent, based on the polymer, of an impact modifier for the polymer;

c. admixing the polymer-impact modifier mixture with from about one-half to about two percent by weight of the polymer of at least one ester of an α-hydroxyacid, the ester containing from above 10 to 25 carbon atoms, no ultraviolet stabilizer being present, so as to distribute the ester essentially uniformly throughout the polymer;

d. forming the polymer-impact modifier-ester mixture into a container, tube, or medical tool;

e. exposing the container, tube, or medical tool to at least about 5 megarads of gamma irradiation or to at least 2.5 megarads of electron beam sterilizing radiation.

* * * * *